United States Patent
Robertson et al.

(10) Patent No.: US 7,073,506 B2
(45) Date of Patent: Jul. 11, 2006

(54) TONGUE STABILIZING DEVICE

(75) Inventors: Christopher John Robertson, Dunedin (NZ); James Thomas Whittington, Dunedin (NZ)

(73) Assignee: Innovative Health Technologies (NZ) Limited, Dunedin (NZ)

( * ) Notice: Subject to any disclaimer, the term of this patent is extended or adjusted under 35 U.S.C. 154(b) by 162 days.

(21) Appl. No.: 10/450,696

(22) PCT Filed: Dec. 15, 2000

(86) PCT No.: PCT/NZ00/00252

§ 371 (c)(1),
(2), (4) Date: Oct. 29, 2003

(87) PCT Pub. No.: WO01/43673

PCT Pub. Date: Jun. 21, 2001

(65) Prior Publication Data

US 2004/0134490 A1  Jul. 15, 2004

(51) Int. Cl.
*A61F 5/56* (2006.01)
(52) U.S. Cl. ................................. 128/848; 128/860
(58) Field of Classification Search ............. 128/848, 128/859, 860, 861, 862
See application file for complete search history.

(56) References Cited

U.S. PATENT DOCUMENTS

| | | | | |
|---|---|---|---|---|
| 4,196,724 A | * | 4/1980 | Wirt et al. | 128/860 |
| 4,198,967 A | * | 4/1980 | Dror | 128/860 |
| 4,834,077 A | * | 5/1989 | Sun | 600/186 |
| 5,373,859 A | * | 12/1994 | Forney | 128/846 |
| 5,465,734 A | | 11/1995 | Alvarez et al. | |
| 6,422,243 B1 | * | 7/2002 | Daram | 128/859 |

* cited by examiner

*Primary Examiner*—Henry Bennett
*Assistant Examiner*—Camtu Nguyen
(74) *Attorney, Agent, or Firm*—Dann, Dorfman, Herrell and Skillman, P.C.

(57) ABSTRACT

A one piece tongue stabilizing device formed of a resiliently flexible material and comprises a body having a hollow interior within which the end of a user's tongue fits and is held by negative pressure. The body of the device comprises an entry portion having an opening to the hollow interior of the device and a bulb portion connected by a narrower diameter neck portion. Tabs extend from the bulb portion which in use engage the exterior of the user's face around the user's mouth or between the user's teeth and lips, to hold the tongue forward to assist in opening user's airway and reducing snoring. A major benefit of the device of the invention is that it does not require specialist fitting or the taking of upper and lower jaw impressions of the patient to produce a tailored device for the patient.

21 Claims, 2 Drawing Sheets

TONGUE STABILIZING DEVICE

FIELD

The invention comprises a tongue stabilising device for use in reducing snoring.

BACKGROUND

Sleep disorders are very common. It has been reported that each year around 50 million report trouble with sleeping and 10 million of them seek medical attention. Inadequate sleep can lead to daytime sleepiness and other sleep related problems.

One form of sleep disorder is sleep apnoea, which is defined as a cessation of airflow greater than or equal to 10 seconds 5 times per hour of sleep time. One form of apnoea is obstructive apnoea which is an absence of airflow due to airway obstruction in the upper airway.

Snoring is created by the vibration of the pharyngeal soft tissues as air passes through an airway that is too small to allow for smooth, unimpeded flow. While obstructive apnoea is marked by total airway closure, snoring is a symptom of partial closure or near collapse. Snoring indicates a partial airway obstruction. That is, as the air flows through a partial obstruction, vibration of tissue occurs, creating the sound of snoring. Many times snoring is a warning sign of impending apnoea. Though some snoring is truly benign and merely obnoxious noise, it has been shown that some instances of loud, regular snoring are associated with true medical morbidity even in the absence of overt obstructive apnoea. Due to the exaggerated breathing effort and noise created by the high resistance to airflow in the upper airway and consequential repetitive arousals from sleep, these heavy snorers may exhibit symptoms common to actual obstructive sleep apnoea. The hallmark of obstructive sleep apnoea is snoring, which is intermittent.

Oral appliance therapy is becoming increasingly popular to treat selected cases of sleep disordered breathing. [1] While not completely effective in all situations, research is showing that oral appliances are very effective in treating snoring in mild obstructive sleep apnoea.

[1] In a preferred form the hollow interior of the device has a general heart shape in cross-section at said neck portion.

U.S. Pat. No. 5,465,734 to Snorex, Inc discloses a tongue retaining device which is typically formed of a flexible polyvinyl material and comprises a hollow interior which fits over the forward end of the tongue and with which the tongue is held forward by negative pressure created with the device. The device has a particular shape, is adjustable in relation to engagement with the users face, and requires specialist fitting or the taking of upper and lower jaw impressions of the patient to produce a tailored device for the patient.

SUMMARY OF INVENTION

The present invention provides an improved, or at least alternative, form of oral therapy appliance useful for eliminating or reducing snoring.

In broad terms the invention comprises a one piece tongue stabilising device formed of a resiliently flexible material and comprising a body having a hollow interior within which the end of a user's tongue fits and is held by negative pressure when the device is fitted on to the user's tongue and which body comprises an entry portion having an opening to the hollow interior of the device and a bulb portion connected by a narrower diameter neck portion, and tabs extending from the bulb portion which in use engage the exterior of the user's face around the user's mouth or between the user's teeth and lips, to hold the tongue forward to assist in opening user's airway and reducing snoring.

Preferably the entry portion is tapered with a reducing diameter from said opening to said neck portion.

Preferably at least the opening and entry portion have a larger cross-sectional dimension across the device.

A major benefit of the device of the invention is that it does not require specialist fitting or the taking of upper and lower jaw impressions of the patient to produce a tailored device for the patient. Rather it is possible to sell the device in a range of a few sizes, over the counter and without requiring special fitting. This is a major advance in terms of cost reduction and ensuring wide spread availability to assist persons with sleep apnoea. This is due to the shape of the device.

BRIEF DESCRIPTION OF DRAWINGS

The accompanying drawings show a preferred form of tongue stabilising device of the invention, by way of example and without intending to be limiting. In the drawings.

DETAILED DESCRIPTION OF PREFERRED FORM

The preferred form of tongue stabilising device comprises a body shaped as shown and also having a hollow interior. The device is formed from a resiliently flexible material and typically a synthetic material such as a polyvinyl material or similar.

The body of the device comprises a hollow bulb portion 2 and an entry portion 3, which are connected by a narrower diameter neck portion 4. The entry portion 3 has an opening into the hollow interior and is tapered with a reducing diameter from the opening to the neck portion 4, so that the neck portion 4 has the narrowest diameter across the device. In the preferred form the shape of the device is such that at least the entry portion and the neck portion are wider across the device than they are in a vertical direction (in orientation of the device during normal use) and the bulb portion 2 may also have a similar shape, but this may not be essential.

Figure 1:
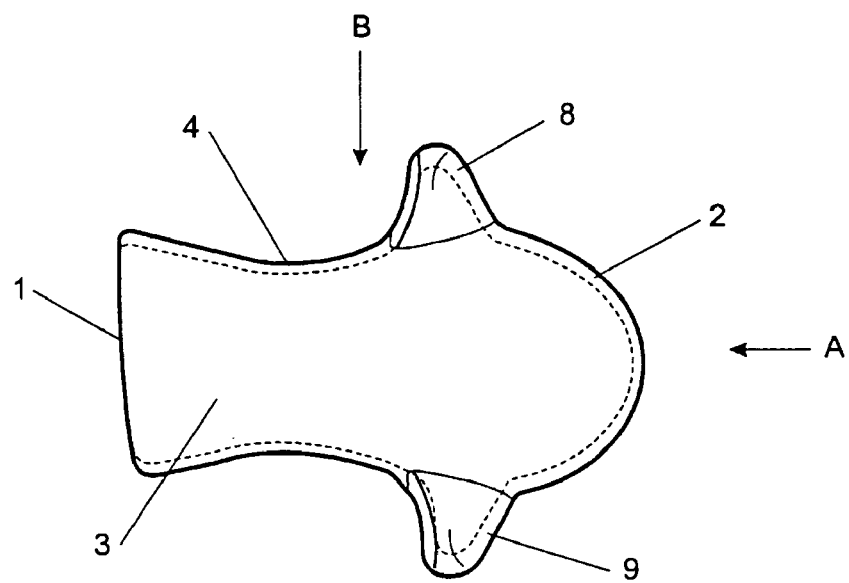
FIG. 1 is a side view of the device.
Figure 2:
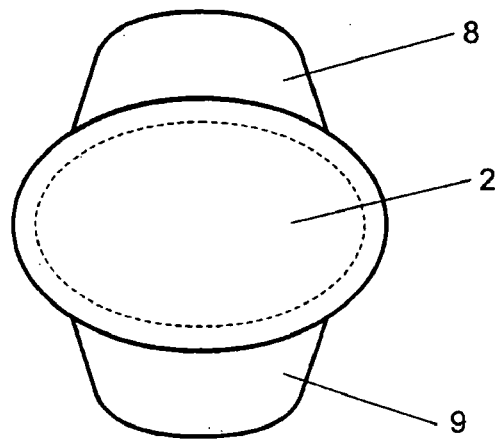
FIG. 2 is a front view of the device in the direction of arrow A in FIG. 1.
Figure 4:
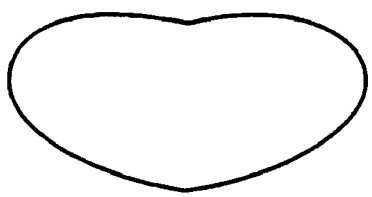
FIG. 4 shows the cross-sectional shape of the device across the neck portion of the device.
Figure 3:
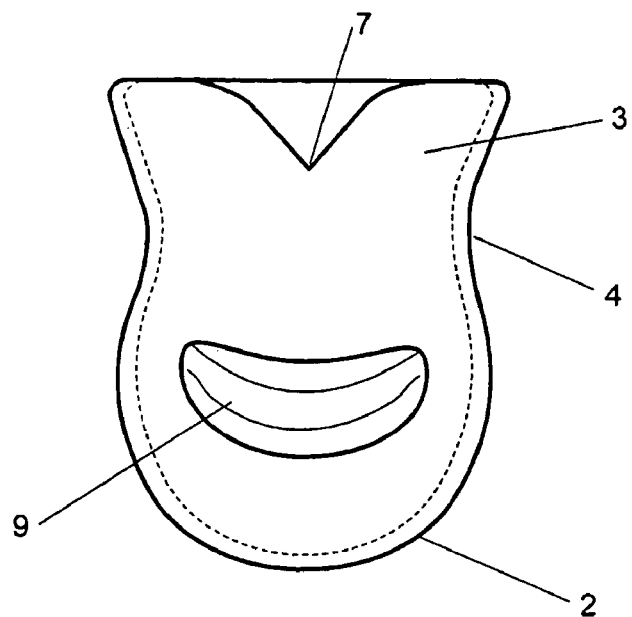
FIG. 3 is a view of the device from below in the direction of arrow B in FIG. 1.
Figure 5:
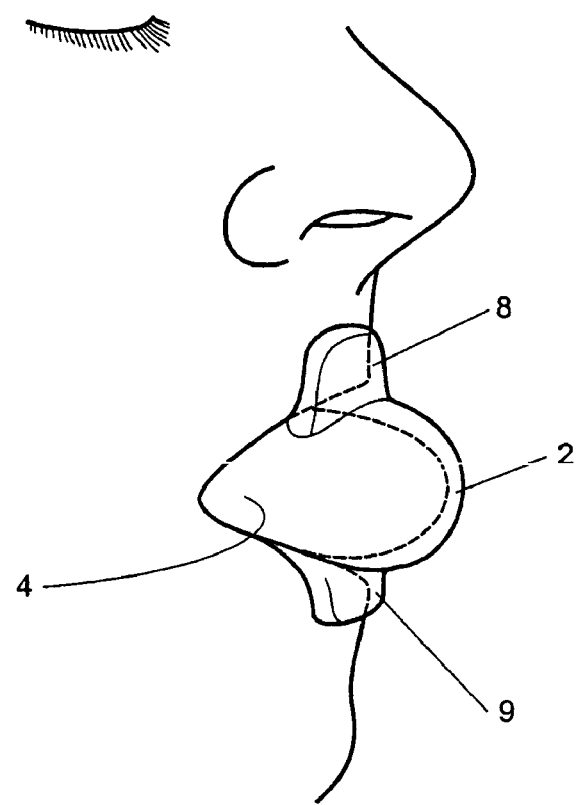
FIG. 5 shows the device in use.

In addition in the preferred form the hollow interior of the device has a heart shape in cross-section at the neck portion, as shown in FIG. 4. Preferably a cut out 7 is formed in the device as shown in FIG. 3 to accommodate the web beneath the user's tongue.

Locating tabs 8 and 9 extend from the top and bottom of the bulb 2. The device is a unitary device with the locating tabs 8 and 9 integrally moulded with the body of the device. Preferably but not essentially the tabs 8 and 9 are also hollow (communicating with the hollow interior of the device and particularly the bulb portion 2), to increase the volume within the device for maximising negative pressure to retain the device on a user's tongue.

In use, the bulb end of the bulb portion 2 of the device is squeezed somewhat and the device is pushed over the end of the user's tongue by the user. The bulb is then released so that it will return to its original shape applying negative pressure within the device to the end of the user's tongue so that the device will be retained on the end of the tongue. In use, the tabs 8 and 9 will then engage the exterior of the user's face, with the upper tab 8 resting against the user's upper lip and the lower tab 9 which is preferably slightly longer as shown resting against the user's lower lip and chin area. Alternatively the tabs 8 and 9 may be positioned slightly further back on the bulb portion from the front end of the bulb portion so that they are positioned to fit between the teeth and lips of the user, and will engage against the user's teeth.

The tongue stabilising device of the invention fits against the mouth or teeth of the user as shown. It may be provided in a number of sizes but because of its shape does not need to be specially fitted or require the taking of upper and lower jaw impressions as with conventional tongue retaining devices. It can therefore be retailed "over the counter" at chemists or pharmacies for example. The device can also be used with edentulous patients.

The foregoing describes the invention including a preferred form thereof. Alterations and modifications as will be obvious to those skilled in the art are incorporated within the scope hereof as defined in the following claims.

The invention claimed is:

1. A one piece tongue stabilising device formed of a resiliently flexible material and comprising a body having a hollow interior within which the end of a user's tongue fits and is held by negative pressure when the device is fitted on to the user's tongue and which body comprises an entry portion having an opening to the hollow interior of the device and a squeezable expanded bulb portion connected by a narrower diameter neck portion, and having a flexible wall section whereby the expanded bulb portion may be squeezed and released in application of the device to a user's tongue, the length dimension of the device from the opening to said entry portion to the narrowest part of said neck portion being shorter than the length dimension of the device from the narrowest part of said neck portion to the distal end of said bulb portion, said body also comprising a cut out into the side wall of the entry portion, and integrally moulded tabs extending from the bulb portion which in use engage the exterior of the user's face or between the user's teeth and lips, to hold the tongue forward to assist in opening user's airway and reducing snoring, said tabs comprising a first tab extending from the exterior of said expanded bulb portion substantially perpendicular to a longitudinal axis of the device.

2. A tongue stabilising device according to claim 1 wherein said entry portion is tapered with a reducing diameter from said opening to said neck portion.

3. A tongue stabilising device according to claim 2 wherein at least said opening and said entry portion have a larger cross-sectional dimension across the device.

4. A tongue stabilising device according to claim 2 wherein the hollow interior of the device has a general heart shape in cross-section at said neck portion.

5. A one piece tongue stabilising device formed of a resiliently flexible material and comprising a body having a hollow interior within which the end of a user's tongue fits and is held by negative pressure when the device is fitted on to the user's tongue and which body comprises an opening to the hollow interior of the device, a squeezable expanded bulb portion, and a narrower diameter neck portion between said opening and said bulb portion and which is tapered with a reducing diameter from said opening to said neck portion and having a flexible wall section whereby the bulb portion may be squeezed and released in application of the device to a user's tongue to create said negative pressure which retains the device on the user's tongue, the length dimension of the device from the opening to said entry portion to the narrowest part of said neck portion being shorter than the length dimension of the device from the narrowest part of said neck portion to the distal end of said bulb portion, and integrally moulded tabs extending from the bulb portion which in use engage the exterior of the user's face, said tabs comprising a first tab extending from the exterior of said bulb portion substantially perpendicular to a longitudinal axis of the device and a second tab extending in substantially an opposition direction to said first tab, one or both of said tabs having a hollow interior which communicates with the interior of the expanded bulb portion, said tabs being shaped and positioned to contact a centre region of a user's upper and lower lips but not over the user's lips in the corner regions of the mouth on either side, to hold the tongue forward to assist in opening the user's airway and reducing snoring.

6. A tongue stabilising device according to claim 1 wherein one or both of said tabs have hollow interior which communicates with the interior of the expanded bulb portion.

7. A one piece tongue stabilising device formed of a resiliently flexible material and comprising of a body having a hollow interior within which the end user's tongue fits and is held by negative pressure when the device is fitted on to the user's tongue and which body comprises an entry portion having an opening to the hollow interior of the device and a squeezable expanded bulb portion connected by a narrower diameter neck portion; and having a flexible wall section whereby the expanded bulb portion may be squeezed and released in application of the device to a user's tongue to create said negative pressure which retains the device on the user's tongue, the length dimension of the device from the opening to said entry portion to the narrowest part of said neck portion being shorter than the length dimension of the device from the narrowest part of said portion to the distal end of said bulb portion, and integrally moulded tabs extending from the bulb portion which in use engage the exterior of the user's face or between the user's teeth and lips, to hold the tongue forward to assist in opening the user's airway and reducing snoring, one or both of said tabs having a hollow interior which communicates with the interior of the expanded bulb portion, said tabs comprising a first tab extending from the exterior of said expanded bulb portion substantially perpendicular to a longitudinal axis of the device and a second tab extending in substantially an opposite direction to said first tab, said tabs being shaped and positioned to contact the user's lips or between the user's teeth and lips in a centre region of a user's upper and lower lips but not over the user's lips or between the user's lips and mouth in the corner regions of the mouth on either side.

8. A tongue stabilising device according to claim 5 wherein at least said opening and said entry portion have a larger cross-sectional dimension across the device.

9. A tongue stabilising device according to claim 8 wherein the hollow interior of the device has a general heart shape in cross-section at said neck portion.

10. A tongue stabilising device and comprising a body having a hollow interior within which the end of a user's tongue fits and is held by negative pressure when the device is fitted on to the user's tongue and which body comprises an entry portion having an opening to the hollow interior of the device and a squeezable expanded bulb portion having a flexible wall section whereby the expanded bulb portion may be squeezed and released in application of the device to a user's tongue to create said negative pressure which retains the device on the user's tongue, the device having a part which engages the user's face to hold the tongue forward to assist in opening the user's airway and reducing snoring wherein said part comprises a first tab extending from the exterior of said expanded bulb portion substantially perpendicular to a longitudinal axis of the device and a second tab extending in substantially an opposite direction to said first tab, the device being a one piece device moulded from a resiliently flexible material with said tabs being integrally moulded with said bulb portion and shaped and positioned to contact the user's lips or between the user's teeth and lips in a centre region of a user's upper and lower lips but not over the user's lips or between the user's lips and mouth in the corner regions of the mouth on either side, and wherein said entry portion is connected to said expanded bulb portion by a narrower diameter neck portion with said entry portion being tapered with a reducing diameter from said opening to said neck portion, said opening and said entry portion being resiliently flexible and having a larger cross-sectional dimension across the device, the hollow interior of the device having a general heart shape in cross-section at said neck portion.

11. A tongue stabilising device according to claim 5 wherein one of said tabs extends from a point on the exterior of said bulb portion closer to said entry portion than the other of said tabs.

12. A tongue stabilising device according to claim 11 wherein said one of said tabs is longer than the other of said tabs.

13. A tongue stabilising device as claimed in claim 10 including a cut-out into the side wall of the entry portion.

14. A tongue stabilising device according to claim 7 wherein said entry portion is tapered with a reducing diameter from said opening to said neck portion.

15. A tongue stabilising device according to claim 7 wherein at least said opening and said entry portion have a larger cross-sectional dimension across the device.

16. A tongue stabilising device according to claim 7 wherein the hollow interior of the device has a general heart shape in cross-section at said neck portion.

17. A tongue stabilsing device as claimed in claim 16 including a cut out into the side wall of the entry portion.

18. A tongue stabilising device according to claim 13 wherein one or both of said tabs have a hollow interior which communicates with the interior of the expanded bulb portion.

19. A tongue stabilising device according to claim 18 wherein one of said tabs extends from a point on the exterior of said bulb portion closer to said entry portion than the other of said tabs.

20. A tongue stabilising device according to claim 19 wherein said one of said tabs is longer than the other of said tabs.

21. A tongue stabilising device according to claim 18 wherein one of said tabs extends from a point on the exterior of said bulb portion closer to said entry portion than the other of said tabs.

* * * * *